United States Patent
Schabert et al.

(10) Patent No.: US 10,238,372 B2
(45) Date of Patent: Mar. 26, 2019

(54) ATRIUM RETRACTOR

(71) Applicant: AESCULAP AG, Tuttlingen (DE)

(72) Inventors: Stefanie Schabert, Aldingen (DE);
Pedro Morales, Tuttlingen (DE);
Thomas Beck, Durchhausen (DE)

(73) Assignee: AESCULAP AG, Tuttlingen (DE)

( * ) Notice: Subject to any disclaimer, the term of this patent is extended or adjusted under 35 U.S.C. 154(b) by 554 days.

(21) Appl. No.: 14/438,790

(22) PCT Filed: Oct. 24, 2013

(86) PCT No.: PCT/EP2013/072241
§ 371 (c)(1),
(2) Date: Apr. 27, 2015

(87) PCT Pub. No.: WO2014/067840
PCT Pub. Date: May 8, 2014

(65) Prior Publication Data
US 2015/0282795 A1 Oct. 8, 2015

(30) Foreign Application Priority Data
Oct. 29, 2012 (DE) .................... 10 2012 219 727

(51) Int. Cl.
*A61B 17/02* (2006.01)
*A61B 17/29* (2006.01)
*A61B 17/00* (2006.01)

(52) U.S. Cl.
CPC .......... *A61B 17/02* (2013.01); *A61B 17/0218* (2013.01); *A61B 2017/00473* (2013.01);
(Continued)

(58) Field of Classification Search
CPC . A61B 17/02; A61B 17/0218; A61B 17/0237; A61B 17/0243
See application file for complete search history.

(56) References Cited

U.S. PATENT DOCUMENTS

| | | | |
|---|---|---|---|
| 6,015,378 A * | 1/2000 | Borst | A61B 17/02 128/898 |
| 2003/0078470 A1* | 4/2003 | Borst | A61B 17/02 600/37 |

(Continued)

FOREIGN PATENT DOCUMENTS

| | | |
|---|---|---|
| WO | 02/28287 A1 | 4/2002 |
| WO | 2007/075903 A2 | 7/2007 |
| WO | 20081098616 A1 | 8/2008 |

OTHER PUBLICATIONS

International Search Report PCT/EP2013/072241 dated Feb. 21, 2014.

*Primary Examiner* — Eric S Gibson
(74) *Attorney, Agent, or Firm* — Kenealy Vaidya LLP

(57) ABSTRACT

The present application discloses an atrium retractor with a plate and a shaft that has a shaft sleeve, an inner rod and an operating mechanism. The operating mechanism is designed to generate a relative movement between the shaft sleeve and the inner rod. An articulation device that is firmly connected either to the plate or the shaft and is detachably connectable to the other from the plate or the shaft is provided in the atrium retractor. The operating mechanism is adapted to optionally lock and release the articulated connection by means of the relative movement between the shaft sleeve and the inner rod.

16 Claims, 3 Drawing Sheets

(52) U.S. Cl.
CPC ............... *A61B 2017/00862* (2013.01); *A61B 2017/0237* (2013.01); *A61B 2017/0243* (2013.01); *A61B 2017/2927* (2013.01)

(56) References Cited

U.S. PATENT DOCUMENTS

| | | | | |
|---|---|---|---|---|
| 2003/0158463 A1* | 8/2003 | Julian | ............... | A61B 17/00234 600/104 |
| 2004/0143163 A1* | 7/2004 | Palmer | ............... | A61B 17/0218 600/204 |
| 2005/0010079 A1* | 1/2005 | Bertolero | ........... | A61B 17/0218 600/37 |
| 2005/0010197 A1* | 1/2005 | Lau | .................... | A61B 17/0206 606/1 |
| 2006/0270909 A1* | 11/2006 | Davis | ................. | A61B 17/0218 600/210 |
| 2008/0281150 A1* | 11/2008 | Wright | ................... | A61B 17/02 600/37 |
| 2010/0286485 A1* | 11/2010 | Valentini | .................. | A61B 1/32 600/224 |
| 2011/0213296 A1* | 9/2011 | Agarwal | ............... | A61B 17/02 604/24 |
| 2012/0078061 A1* | 3/2012 | Calafiore | ........... | A61B 17/0206 600/229 |
| 2012/0157788 A1* | 6/2012 | Serowski | ........... | A61B 17/0206 600/229 |
| 2015/0182225 A1* | 7/2015 | Morejohn | ........ | A61B 17/12013 606/144 |
| 2015/0282795 A1* | 10/2015 | Schabert | ........... | A61B 17/0218 600/213 |
| 2015/0297347 A1* | 10/2015 | Morales | ................ | A61B 17/02 600/37 |
| 2016/0030031 A1* | 2/2016 | Vogtherr | ................ | A61B 17/02 600/37 |
| 2017/0000508 A1* | 1/2017 | Halkos | ............... | A61B 17/0218 |

* cited by examiner

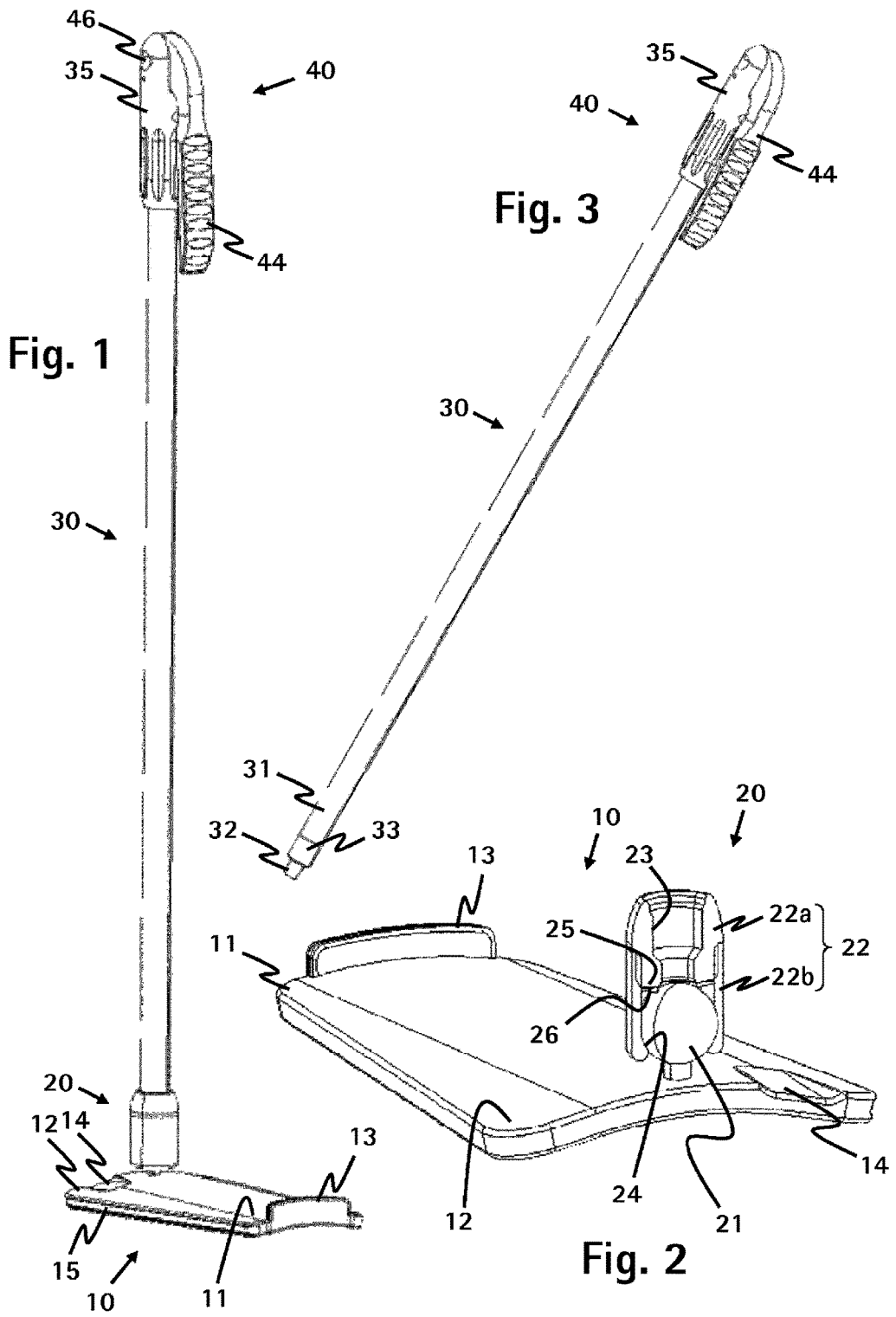

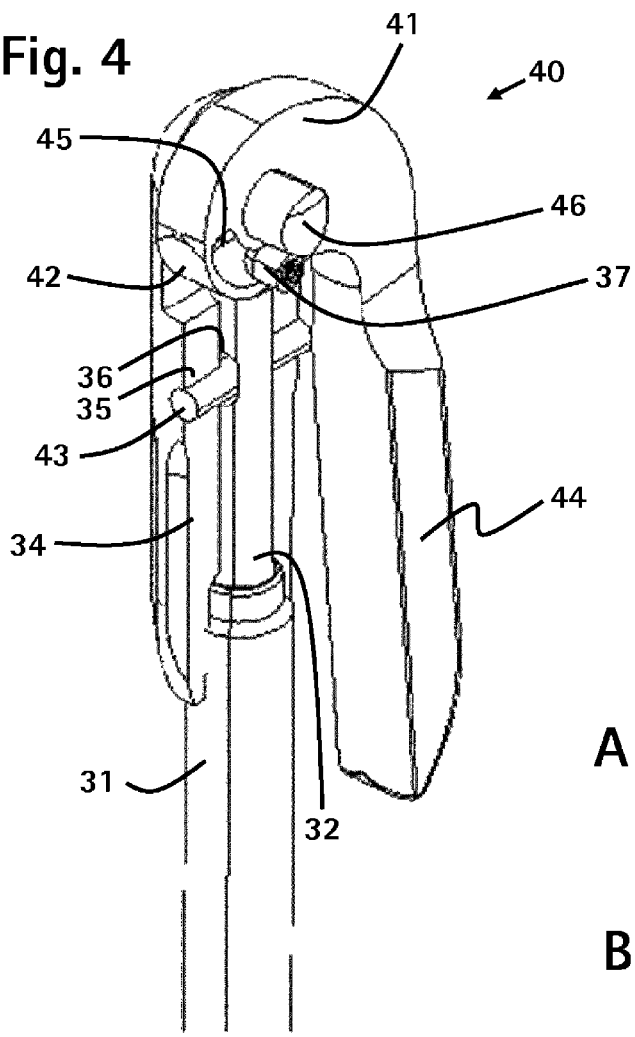
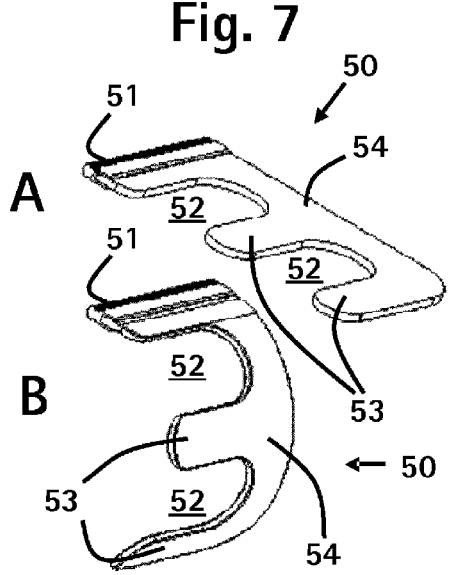
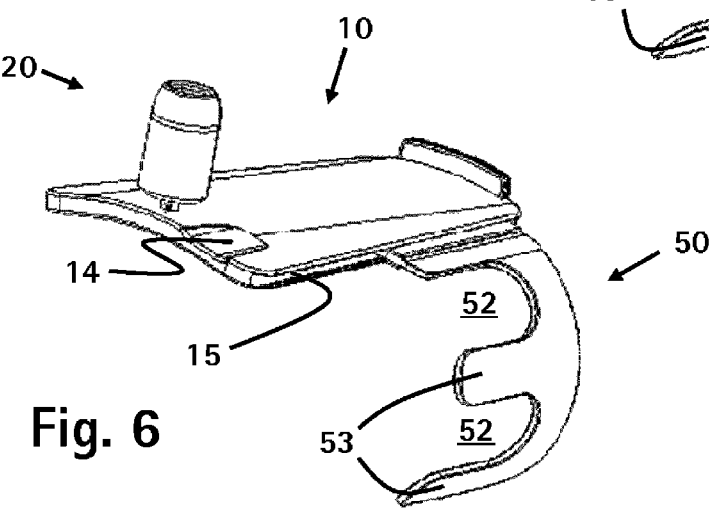

ATRIUM RETRACTOR

The present invention relates to an atrium retractor, that is, a device for lifting the ventral wall of a right atrium of a heart.

STATE OF THE ART

In some heart surgeries, the heart must be brought into specific positions in order to provide an access for the surgeon to the surgical field. If an access to the rear of the heart has to be ensured, the heart is lifted. If one wishes to operate on the tip of the heart, a surgical drape can, for example, be pushed under the heart, and the heart then partially lies on it and is thus moved into an elevated position. There are also devices for suctioning the tip of the heart with a vacuum and thereby allowing the heart to be elevated.

Furthermore, there are devices which elevate a specific part of the heart. In an operation on the mitral valve, the left heart ventricle is cut open, and the ventral wall of the left atrium is elevated in order to create and access to the mitral valve. In the international patent application WO 2008/098616, an atrium lift or an atrium retractor is disclosed that possesses a curved plate which is pivoted on an elongated shaft. The angle between the plate and the shaft can be adjusted by means of an actuating device on the shaft. In this manner, the plate can be aligned with the longitudinal axis of the shaft and can hence be inserted through an incision into the chest of a patient. The plate is then moved by means of the actuating device to a position in which the plate is aligned substantially perpendicular to the longitudinal axis of the shaft. The plate can then be introduced into the open atrium of the heart, and the ventral wall can be lifted. The disadvantage of this prior art is that a very large incision must be made close to the heart in order to introduce the plate into the body of the patient. Since the plate is also curved, two neighboring ribs must be spread with the assistance of an additional retractor in order to introduce the retractor close to the heart.

US patent application U.S. 2004/0143163 also discloses an endoscopic atrium lift or an atrium retractor wherein the plate consists of segments which are articulated to each other and can be rolled together in order to introduce the retractor into the body of the patient and remove it so that they assume a minimum diameter. The disadvantages of this device are, however, that a relatively large incision is required close to the heart in order to introduce the rolled-up plate through it. In addition, the mechanical system which rolls up and rolls together the plate locks at least partially the free view on the mitral valve. The ventral wall of the atrium must therefore be excessively elevated in order to expose an adequate visual field and a sufficient access.

The object of the present invention is therefore to create an atrium retractor with the assistance of which a free visual field of the mitral valve and a large access thereto can be created without requiring a large incision close to the heart.

An additional object of the present invention is to create an atrium retractor that enables improved mobility of the plate relative to the shaft of the retractor.

The object of the present invention is achieved by means of an atrium retractor according to claim 1. Advantageous embodiments and further developments of the atrium retractor according to the invention are the subject matter of the dependent claims.

The atrium retractor according to the invention has a plate and a shaft, wherein the shaft has a shaft sleeve, an inner rod, and an operating mechanism. The operating mechanism is designed such that it can effect a relative movement between the shaft sleeve and the inner rod. An articulation device is furthermore firmly connected either to the plate or the shaft, and it can be detachably connected to the other from the plate or the shaft. This means that the articulated connection is firmly mounted on one component and detachably mounted on the other component. It does not matter whether the firm connection is inseparable as for example is the case with a material connection by welding, but rather whether the connection is firm enough to not be detached accidentally when the detachable connection to the other component is to be detached. If both connections are for example threaded connections, then the firm connection should for example be secured with a locknut so that this connection does not detach when the detachable connection is detached. The operating mechanism is furthermore adapted to optionally lock and release the articulated connection by means of the relative movement between the shaft sleeve and the inner rod.

It is irrelevant whether the articulated connection is locked or released when the operating mechanism is in an actuated state and is correspondingly released or locked when the operating mechanism is in a non-actuated state. With such an atrium retractor, it is possible to change the position of the plate relative to the shaft when the articulated connection is released, and to secure the position between the shaft and plate when the articulated connection is locked. The plate can accordingly assume and retain numerous positions relative to the shaft. In order to precisely adjust the position of the plate relative to the shaft, the plate is for example gripped by a conventional needle holder and moved relative to the shaft that is at least either held by a hand of surgeon or an assistant, or is fastened to a holding device until a desired position is reached. Then the articulation mechanism is locked so that the position of the plate is fixed relative to the shaft.

In an operation on the mitral valve, an incision is made between two neighboring right ribs of the patient, generally between the fifth and sixth right ribs, and this incision and the associated ribs are spread by means of a conventional retractor. From this access, the surgeon has a view of the subsequent surgical field of the heart and mitral valve, and performs the operation. Then the left heart ventricle is cut open. In order to be able to elevate the ventral wall of the heart ventricle, an additional small incision is made directly next to the heart from the front into the chest. This incision can be very small and does not have to be spread by a retractor since only the distal end of the shaft of the atrium retractor must be guided through at that location. The plate is introduced through the larger opening on the right side of the chest and guided to the heart with the assistance of a needle holder or comparable instrument. Then the distal end of the shaft is introduced through the small frontal incision and coupled to the plate. Then the surgeon adjusts the desired position between the plate and shaft and locks the articulated connection. To adjust the desired position of the plate and for any corrections in the position during the operation, the plate is preferably firmly held by an instrument such as a needle holder. The surgeon can then push the plate of the atrium retractor between the ventral and dorsal wall of the heart ventricle and advance it out of the ventral wall of the heart ventricle by pulling the shaft slightly out of the chest of the patient.

If the retractor is no longer needed, the plate can again be gripped by an instrument, and the detachable connection between the articulated connection of the plate or the shaft is detached. The shaft is then pulled forward out of the chest, possibly together with the articulated connection, and the plate is removed laterally through the opening in the right chest (also possibly together with the articulated connection).

According to an advantageous embodiment of the present invention, the operating mechanism is adapted to optionally lock the relative movement between the shaft sleeve and inner rod by means of a friction lock. A friction lock as a locking mechanism is advantageous since it can be realized independent of the position of the plate relative to the shaft and enables smooth adjustment. With form-fit locking mechanisms, smooth adjustment is impossible or only very difficult; nevertheless, form-fit locking mechanisms are feasible, especially when there are a specific number of preferred positions of the plate with regard to the shaft.

According to an additional advantageous embodiment of the present invention, the articulated connection is firmly connected to the plate, and is detachably connectable to the shaft. This means that the articulation device is introduced into the chest and removed from the chest together with the plate. In this manner, the frontal incision (i.e., the incision runs in the frontal plane of the patient, i.e., in the front of the chest) can be further minimized. In this embodiment, the articulated connection has a first component that is rigidly fixed to the plate and a second component that is movable and especially pivotable relative to the plate. The articulated connection is correspondingly formed for example by a hinge joint, a saddle joint or a ball joint. With a hinge joint, an adjustment of the position of the plate relative to the shaft about one axis is possible, with a saddle joint, an adjustment about two axes is possible, and with a ball joint, an adjustment about even three axes is possible; in comparison to a saddle joint, the plate can hence also be rotated relative to the shaft about the shaft axis.

According to another advantageous embodiment of the present invention, the articulated connection has a ball joint connection comprising a joint ball and a ball sleeve. With such a ball joint connection, a particularly free adjustment of the position of the plate relative to the shaft is enabled. The joint ball is thereby fixed on the plate, and the ball sleeve has a thread. The shaft sleeve also has a thread and can be screwed into the thread of the ball sleeve. In this manner, the detachable connection between shaft and the articulated connection or the plate is established. The inner rod is furthermore a push rod which is adapted to exert pressure on the joint ball when the operating mechanism is in an actuated state in order to press the joint ball against a seat which is formed on the joint sleeve in order to lock the articulated connection. Alternately in the present embodiment of the articulated mechanism as a ball joint connection, the inner rod can be a pull rod and connected to the joint ball.

According to another further advantageous embodiment of the present invention, a support is provided in the ball sleeve against which an elastic element is braced that is arranged between the ball housing and joint ball in order to press the joint ball by a predetermined force against the seat when the articulated connection is in a released state. In this manner, uncontrolled movement of the ball sleeve relative to the plate is prevented. This yields the advantage that the distal end of the shaft can be more easily introduced into the opening in the joint sleeve since this cannot so easily escape the shaft end. Furthermore, it is advantageous if the joint sleeve cannot rotate about its axis relative to the plate without force since, in this case, the shaft or the shaft sleeve could only be screwed in if the joint sleeve were firmly held. This would have to be done with an additional instrument which is difficult and complicated given the limited space. The elastic element is preferably a spring, and especially a leaf spring or disc spring. Especially with a disk spring, the joint sleeve can be dimensioned small, and sufficient force can simultaneously be exerted on the ball in order to achieve friction between the joint ball and joint sleeve which enables the shaft sleeve to be screwed into the joint sleeve.

According to an advantageous embodiment of the present invention, the joint sleeve has two parts that are separably or inseparably connected to each other. The seat and support are preferably provided on different parts of the joint sleeve. Individual parts can hence be easily produced, and assembly of the articulation device is hence very easy.

According to one particularly advantageous embodiment of the present invention, the plate is curved, and/or a laterally running projection is provided on its distal end and projects from the plate in a ventral direction during use of the atrium retractor. Given the lateral curve of the plate, it is adapted particularly well to the anatomical conditions of the ventral heart ventricle wall. The laterally running projection serves to prevent accidental slippage of the heart ventricle wall from the plate.

According to another particularly advantageous embodiment of the present invention, the plate has a gripping area that is adapted to be gripped by an instrument. As described above, the plate is inserted laterally into the chest over a relatively long distance. In order to keep this incision as small as possible and in order to transport the plate in a controlled manner through the chest, it is gripped and guided at least with one instrument such as a needle holder. The gripping area is preferably designed so that swinging, i.e., lateral rotation, of the plate relative to the instrument is prevented. The gripping area is designed for example as an area on the proximal end of the plate, the thickness of which is reduced relative to the other plate. If the plate seeks to rotate laterally relative to the instrument by means of which it is introduced, the lateral walls of the gripping area contact the jaws of the instrument. In this manner, rotation of the plate relative to the instrument is prevented or at least limited. Alternately, the gripping area can also be defined by the lateral limits in the form of projections or the alike.

According to another advantageous embodiment of the present invention, the atrium retractor has at least one expansion plate that can be separably affixed to the plate of the retractor. The plate in the area of at least one lateral edge has a groove in which a spring of the expansion plate can be inserted so that the plate and the expansion plate basically form a common plate surface. The expansion plate is inserted in the groove in the plate preferably from the rear end of the plate, i.e., opposite the end on which the laterally running projection is arranged in a few cases. In addition, the groove is preferably narrow or closed at the front end of the plate so that the expansion plate cannot be pushed forward out of the groove in the plate.

According to a particularly advantageous embodiment of the present invention, the at least one groove is formed in the lateral side surface of the plate. In this manner, a particularly soft transition is created from the outer surface or top surface of the plate to the outer surface or top surface of the expansion plate. In addition, the field of view of the surgical area is restricted as for example would be the case if the groove were arranged on the bottom side of the plate.

According to another advantageous embodiment of the present invention, the expansion plate is adapted to be plastically flexible in a lateral direction. This is enabled in that the expansion plate is formed from at least one partially plastic material such as sheet metal. The thickness and material of the sheet metal are chosen so that the expansion plate can be bent by the muscular force of the surgeon, or with the assistance of forceps or the like. The plate preferably has at least one cutout that extends from its rear edge to the front area of the expansion plate. In this case, the expansion plate is particularly easy to bend in the area of the cutouts; simultaneously, however, the shielding effect of the expansion plate is only minimally impaired. The ventral wall of the heart ventricle is muscle tissue that has a certain firmness. Consequently, the tissue in the area of the cutouts does not enter far into the shielded area within or below the expansion plate.

According to one advantageous embodiment of the present invention, the operating mechanism is an eccentric lever with an eccentric surface, wherein the eccentric lever is articulated to the shaft sleeve, and its eccentric surface lies against the proximal end of the push rod. Alternatively, a rotary link can be provided as the operating mechanism which, when it rotates about the longitudinal axis of the shaft, causes the shaft sleeve to shift relative to the inner rod. An eccentric lever is however advantageous in that it enables a quick transition from the released position to the locked position of the articulation device. Furthermore, an eccentric lever is also suitable for actuation with only one hand and for applying great force. If in addition the shaft is mounted in the articulated section by means of a thread, the maximum applicable force by the eccentric lever can be adjusted thereby so that the shaft can be screwed into the thread to different depths. In this manner, excessive wear can also be prevented since great clamping force does not have to be applied merely to close the eccentric lever. In this case, the shaft can simply be screwed slightly out of the thread which reduces the force applied when the eccentric lever is in the closed position.

According to another advantageous embodiment of the present invention, the eccentric lever is fastened to the shaft sleeve by means of a handle sleeve. The handle sleeve has a through-hole, and the push rod has a slot. The slot can, in principle, also be a round hole with a diameter that is greater than that of the pin which extends through the through-hole in the handle sleeve and the slot or round hole in the push rod. It is only important for there to be a certain mobility between the slot or round hole so that the handle sleeve (and hence the shaft sleeve) and push rod can move toward each other in an axial direction. In this manner, maximum movement of the push rod is limited relative to the shaft sleeve, especially when the operating mechanism is in a non-actuated state. This can for example prevent the actuating arm of the eccentric lever from moving to the opposite side of the shaft and possibly being incorrectly actuated.

According to another advantageous embodiment of the present invention, the eccentric lever has an actuating arm that, when the operating mechanism is in an actuated state, runs substantially parallel to the shaft sleeve and preferably lies substantially against the shaft sleeve. This is particularly advantageous for single-handed actuation since the path of movement of the actuating arm can be close to the shaft which also has to be grasped for actuation. In addition, the arrangement of the actuating arm close to the shaft reduces the danger of someone or something getting tangled in the actuating arm so that the atrium retractor unintentionally moves, rotates or even releases the articulation device.

According to an advantageous embodiment of the present invention, the handle sleeve has a projection which engages in a groove that is provided in the eccentric lever, and extends in a circular arc around the rotational center of the eccentric lever in order to limit the rotary movement of the eccentric lever relative to the shaft sleeve. This feature also serves to render the actuation and mounting of the atrium retractor more reliable in that the actuating handle cannot swing to the opposite side of the shaft and then perhaps be improperly actuated. Preferably, this projection is formed by a spring-loaded ball that runs in the groove, and the groove has a recess at the location at which the ball is in the groove when the eccentric lever is basically opened completely. In this manner, the eccentric lever is held in the open position by the spring-loaded ball until force is applied to the eccentric lever by the user that overcomes the spring force of the spring and which pushes the ball toward the groove.

According to another advantageous embodiment of the present invention, the atrium retractor has a support foot or support plate that is attached or attachable to the shaft and is adapted to brace against an area of the patient's chest. In this manner, the atrium retractor does not have to be held by an assistant. Furthermore, it can be positioned more precisely. It is, however, even more advantageous if the atrium retractor can be mounted on a holding device, for example on another retractor or on the operating table. It is also feasible for the atrium retractor to be mounted indirectly on the operating table.

Further advantages and characteristics of the invention are apparent to the person skilled in the art from the attached figures and the detailed description of the exemplary embodiments.

FIG. 1 shows an isometric view of an atrium retractor according to an exemplary embodiment of the present invention;

FIG. 2 shows an isometric view of the plate of the atrium retractor of FIG. 1 with a partially cut-away articulation device;

FIG. 3 shows an isometric view of a shaft of the atrium retractor of FIG. 1;

FIG. 4 shows an perspective view of a handle section of the shaft of FIG. 1 with a partially cut-away handle sleeve;

FIG. 6 shows an isometric view of the plate and expansion plate of FIG. 5; and

FIG. 7 shows an expansion plate according to FIG. 5, wherein dig. 7A shows the plate in an initial state, and FIG. 7B shows the plate in an appropriately bent-back state.

Figure 5:
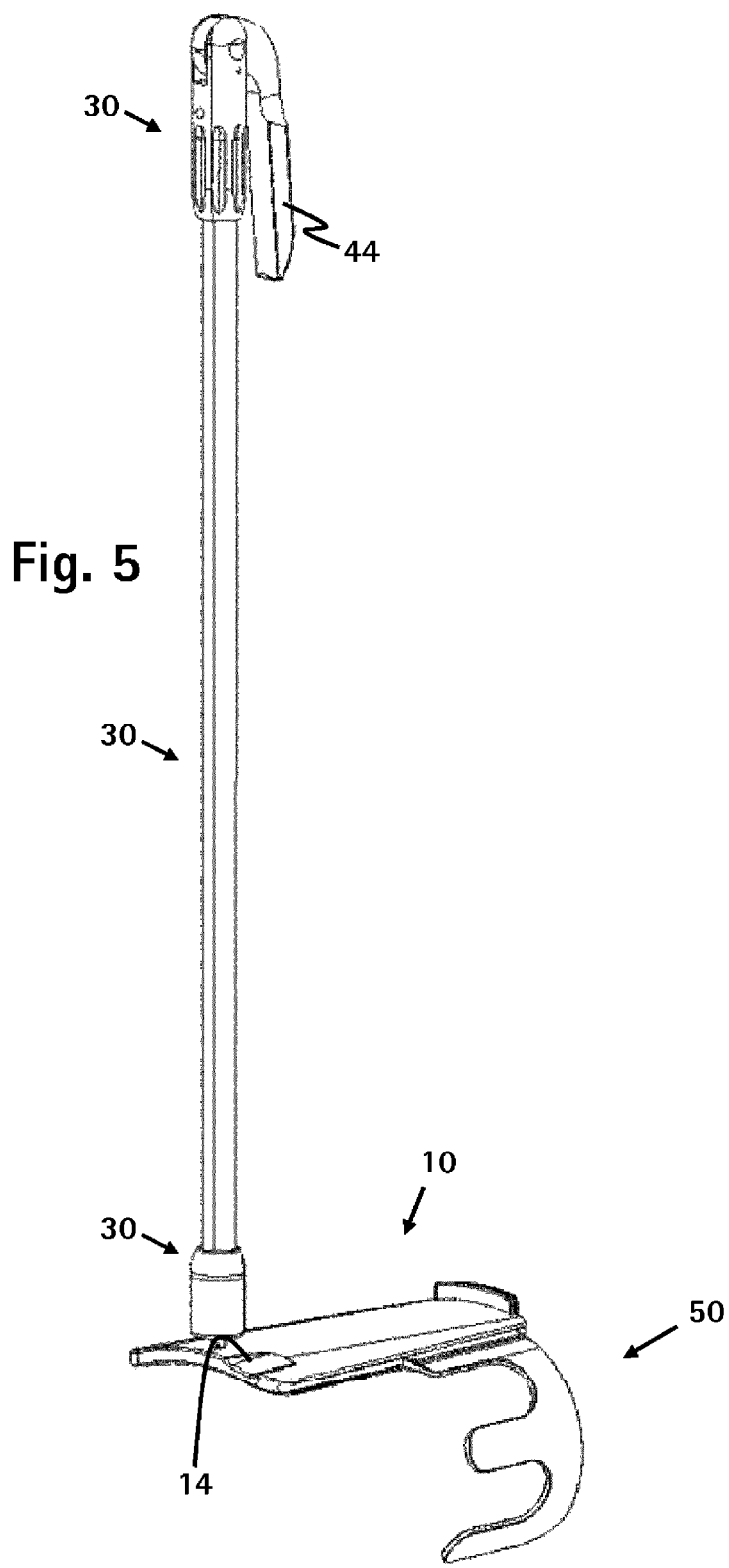
FIG. 5 shows an isometric view of the atrium retractor of FIG. 1 with an expansion plate.

An exemplary embodiment of the present invention is described in detail below with reference to the figures.

The atrium retractor according to this exemplary embodiment has a plate 10 and a shaft 30 that has a shaft sleeve 31, a push rod 32 and an operating mechanism 40. The operating mechanism 40 is designed to generate a relative movement between the shaft sleeve 31 and the inner rod 32. A ball joint connection 21, 22 which has a joint ball 21 and a ball sleeve 22 is firmly connected to the plate 10. Stated more precisely, the joint ball 21 is firmly connected to the plate 10, and the joint sleeve 22 possesses a thread 23 into which an outer thread 33 can be screwed that is formed on the distal end of the shaft sleeve 31.

In the joint sleeve 22 which consists of two components 22a, 22b, a support is provided on the component 22a against which a disk spring 26 abuts. At its opposite side, the disk spring 26 abuts the joint ball 21 and, when the articulated connection 20 is in a released state, presses the joint ball 21 with a predetermined force against the seat 24 which is provided on the other component 22a of the joint sleeve 22. In this manner, uncontrolled movement is prevented of the joint sleeve 22 relative to the plate 10, and hence uncontrolled movement of the plate 10 relative to the shaft 30.

The plate 10 of the atrium retractor is curved, and its front end 11 has a laterally running projection 13 that projects from the plate 10 in a ventral direction, i.e., toward the inside of the ventral wall of the ventricle, when the atrium retractor is used. Furthermore, the plate 10 has a gripping area 14 on its rear end 12 which is adapted to be gripped by an instrument. The gripping area of 14 is designed in this instance as a location at which the plate 10 has a thickness that is less than other places. Side walls are thereby formed on the gripping area that can contact the branches of the instrument which grip the plate and thereby prevent the plate from rotating laterally relative to the instrument.

In addition, the atrium retractor in this exemplary embodiment has an expansion plate 60 that is detachably attachable to the plate 10 of the atrium retractor. In its right, lateral side surface, the plate 10 has a groove 15 into which a spring 51 of the expansion plate 50 can be inserted. The plate 10 and the expansion plate 50 thereby basically form a common plate surface. The expansion plate 50 is flat in its initial position and is adapted to be plastically bent in a lateral direction, for example by a surgeon or his assistant. The expansion plate can however also be delivered with a certain curve so that only minor adaptations to the individual conditions in the surgical area by the surgeon are necessary. The expansion plate 50 has two cutouts 52 that extend from the rear edge to the front area 54 of the expansion plate 50. The fingers 53 which are thereby formed project toward the rear from the front area 54 to the rear end 12 of the plate. The fingers 53 in this case are shorter than the plate 10 and can, however, have the same length as the plate 10. The groove 15 in the plate 10 is closed at its front end so that the expansion plate 50 cannot be pushed forward out of the groove 15.

The operating mechanism 40 is formed by an eccentric lever 41 with an eccentric surface 42. The eccentric lever 41 is articulated to the handle sleeve 35 which in turn is fastened to the shaft sleeve 31. The eccentric surface 42 lies against the proximal end of the push rod 32 and presses the push rod 32 in an actuated state, i.e., in the position shown in FIG. 4, towards the joint ball 21 so that the plate 10 is firmly held against the shaft by a friction lock between the push rod 32 and the joint ball 21, but especially by the friction lock between the joint ball 21 and the seat 24.

The handle sleeve 34 has a through-hole 35, and the push rod has a slot 36. A pin 43 extends through the through-hole 35 in the handle sleeve 34 and the slot 36 into the push rod 32 and thereby limits the maximum movement of the push rod 32 relative to the shaft sleeve 31. The eccentric lever 41 has an actuating arm 44 which, when the operating mechanism 40 is an actuated state, runs substantially parallel to the shaft sleeve 31. The actuating lever does not lie against the shaft sleeve 31 but only leaves a slight gap between itself and the shaft sleeve 31. The handle sleeve 35 possesses a projection 37 which engages in a groove 45 that is provided in the eccentric lever 41 and extends in a circular arc about the rotational center 46 of the eccentric lever 41. In this exemplary embodiment, the projection 37 consists of a spring and a ball, wherein the spring pretensions the ball against the groove 45. The ball can only move axially relative to the hole in which the spring is arranged. If the ball 37 contacts the side end walls of the groove 45, this contact limits the rotary movement of the eccentric lever 41 relative to the shaft sleeve 31. At the place where the ball is located when the eccentric lever 45 is basically completely open, the groove 45 also has a recess. The ball is pressed into the recess by a spring when the eccentric lever 41 is basically completely open and thereby holds the eccentric lever 41 in this position. The surgeon can then adjust the position of the shaft relative to the plate without having to hold the eccentric lever 41 in the open position. In order to close the eccentric lever 41, first the force must be overcome with which the spring presses the ball into the groove 45.

The present atrium retractor can also be fastened to a holding device. Conventional fastening means (not shown) can be used for this.

The above-described invention can be designed and modified in many ways, and the specifically described embodiment is not to be understood as restricting the scope of protection as defined in the claims.

The invention claimed is:

1. An atrium retractor, comprising:
   a plate,
   a shaft that has a shaft sleeve, an inner rod that is a push rod and an operating mechanism, wherein the operating mechanism is designed to effect a relative movement between the shaft sleeve and the inner rod, and
   an articulation device which is firmly connected to the plate and is detachably connected to the shaft, the articulation device including an articulated connection that includes a joint ball and a ball sleeve, wherein the joint ball is fixed on the plate, and
   wherein the operating mechanism is adapted to lock and release the articulation device by the relative movement between the shaft sleeve and the inner rod, and
   wherein the operating mechanism is an eccentric lever with an eccentric surface, wherein the eccentric lever is articulated so as to press the push rod into an actuated state so that the plate is held against the shaft by a friction lock.

2. The atrium retractor according to claim 1, wherein the operating mechanism is adapted to lock the relative movement between the shaft sleeve and the inner rod by friction lock.

3. The atrium retractor according to claim 1, wherein the articulated connection has a first component that is rigidly fixed to the plate and a second component that is movable and pivotable relative to the plate.

4. The atrium retractor according to claim 3, wherein the articulated connection is a ball joint connection that has the joint ball and the ball sleeve, wherein
   the ball sleeve has a thread,
   the shaft sleeve has a thread and can be screwed into the thread of the ball sleeve, wherein
   the inner rod is the push rod which is adapted to exert pressure on the joint ball when the operating mechanism is in an actuated state in order to press the joint ball against a seat which is formed on the joint sleeve in order to lock the articulated connection.

5. The atrium retractor according to claim 4, wherein
   a support is provided in the joint sleeve that abuts an elastic element which, on an opposite side, abuts the joint ball in order to press the joint ball against a seat with a predetermined force when the articulated connection is in the released state in order to prevent an uncontrolled movement of the joint sleeve relative to the plate, wherein the elastic element is one of a spring, a leaf spring and disk spring.

6. The atrium retractor according to claim 4, wherein the joint sleeve has two parts which can be separately or inseparably connected to each other, wherein the seat and the support are provided on different parts of the joint sleeve.

7. The atrium retractor according to claim 4, wherein the eccentric lever is articulated to the shaft sleeve, and the eccentric surface lies against a proximal end of the push rod.

8. The atrium retractor according to claim 7, wherein the eccentric lever is fastened by a handle sleeve to the shaft sleeve,
the handle sleeve has a through-hole, and
the push rod has a slot, wherein a pin extends through the through-hole in the handle sleeve and the slot in the push rod to thereby limit a maximum movement of the push rod relative to the shaft sleeve, especially when the operating mechanism is in a non-actuated state.

9. The atrium retractor according to claim 7, wherein the eccentric lever has an actuating arm that runs parallel to the shaft sleeve when the operating mechanism is in an actuated state, and lies substantially on the shaft sleeve.

10. The atrium retractor according to claim 7, wherein the handle sleeve possesses a projection which engages in a groove that is provided in the eccentric lever and extends in a circular arc about the rotational center of the eccentric lever in order to limit the rotary movement of the eccentric lever relative to the shaft sleeve.

11. The atrium retractor according to claim 1, wherein the plate is curved and/or its front end has a laterally running projection that projects from the plate in a ventral direction when the atrium retractor is used.

12. The atrium retractor according to claim 1, wherein the plate has a gripping area which is adapted to be gripped by an instrument, wherein the gripping area is designed to prevent the plate from swinging relative to the instrument.

13. The atrium retractor according to claim 1, including at least one expansion plate which is separably affixable to the plate of the atrium retractor,
wherein
the plate in the area of at least one lateral edge has a groove in which a spring of the expansion plate is inserted so that the plate and the expansion plate form a common plate surface.

14. The atrium retractor according to claim 13, wherein the at least one groove is formed in a lateral side surface of the plate.

15. The atrium retractor according to claim 13, wherein the expansion plate is adapted to be plastically bendable in a lateral direction, wherein the expansion plate has at least one cutout that extends from a rear edge to a front area of the expansion plate.

16. The atrium retractor according to claim 1, further comprising
a support foot or support plate that is attached or attachable to the shaft and is adapted to brace against an area of the patient's chest.

* * * * *